United States Patent [19]

Kasper

[11] 4,356,263

[45] Oct. 26, 1982

[54] METHOD OF MAKING A POLYSACCHARIDE VACCINE

[75] Inventor: Dennis L. Kasper, Newton Center, Mass.

[73] Assignee: President and Fellows of Harvard College, Cambridge, Mass.

[21] Appl. No.: 316,544

[22] Filed: Oct. 29, 1981

Related U.S. Application Data

[60] Division of Ser. No. 157,859, Jun. 9, 1980, Pat. No. 4,324,887, which is a continuation-in-part of Ser. No. 934,214, Aug. 16, 1978, Pat. No. 4,207,414.

[51] Int. Cl.$^3$ .............................................. C12P 19/04
[52] U.S. Cl. .................................... 435/101; 435/885
[58] Field of Search ........................... 435/101; 424/88

[56] References Cited

PUBLICATIONS

Baker et al., "J. of Exptal. Medicine", vol. 143, pp. 258–269, 1976.
Baker et al., "Infection and Immunity", vol. 13, pp. 189–194, 1976.
Baker et al., "J. Clinical Investig.", vol. 59, pp. 810–818, 1977.
Baker et al., "J. Clinical Investig.", vol. 61, pp. 1107–1110, 1978.
Baker et al., "Chem. Abst.", vol. 88, #25, 187967(c), 1978.
Kasper et al., "Jour. of Immunology", vol. 121, #3, pp. 1096–1105, 1978.
Yokomizo et al., "Chem. Abst.", vol. 88, #21, 150485(t), 1978.
Leslie et al., "The J. of Immunology", vol. 110, #1, pp. 191–196, 1973.

*Primary Examiner*—Lionel M. Shapiro

[57] ABSTRACT

Culturing *Streptococcus agalactiae* in a nutrient broth containing at least 10 g/l of glucose while maintaining the pH at 6–8 by the addition of alkaline material produces polysaccharide antigen including a fraction having a molecular size from $8-11\times 10^5$d. By employing a broth free from constituents having a molecular size above $10^5$, the antigens can be separated from the broth in high yield after harvesting the organisms. Vaccination of humans with *Streptococcus agalactiae* polysaccharide antigens having molecular sizes above $5\times 10^5$ produces in selected individuals specific antibody levels above 200 µg/ml of antisera; globulins fractionated from such antisera contain most of the antibody and can be used for passive immunization.

19 Claims, No Drawings

METHOD OF MAKING A POLYSACCHARIDE VACCINE

This is a division, of application Ser. No. 157,859, filed June 9, 1980, now U.S. Pat. No. 4,324,887, issued Apr. 13, 1982, which is a continuation-in-part of copending application Ser. No. 934,214 filed Aug. 16, 1978, now U.S. Pat. No. 4,207,414.

The invention described herein was made in the course of work under a grant or award from the Department of Health, Education and Welfare.

This invention relates to a method of making a polysaccharide antigen or vaccine against *Streptococcus agalactiae* (hereinafter called Group B streptococcus), to the antigen or vaccine thus prepared and to a method of making and using a highly active immunoglobulin antibody useful for passive immunization against such organisms.

It has previously been proposed to prepare a Type III polysaccharide of Group B streptococci by culturing the organisms in Todd-Hewitt broth containing 2 g/l of glucose and buffered at pH 6.5-7.4, separating the organisms from the broth, then extracting the polysaccharides from the organisms. However, the polysaccharides prepared in this manner are obtained only in low yield, and are reactive only with Type III-specific antisera. Baker, Kasper and Davis, The Journal of Experimental Medicine, Vol. 143, 258-269 (1976). It has been proposed to increase the concentration of glucose in the growth medium and increase the buffering capacity to increase the yield of polysaccharides, Baker and Kasper, Infection and Immunity, Vol. 13, pages 189-194 (1976). It has also been proposed to isolate naturally-occurring antiserum from the blood of humans infected by live Group B streptococci, but the immunological activity of such antisera has been generally very slight.

It has now been found that polysaccharide antigens having a large molecular size fraction ($0.8-6 \times 10^6$ d) of increased immunogenicity and distinctly different in chemical composition from those previously prepared can be made by culturing or propagating a Group B streptococcus in a nutrient broth containing a high concentration of glucose, preferably 10-15 g/l or more, and by maintaining the pH of the broth at pH 6-8, preferably 6.8-7.6, throughout the culturing. The term "molecular size" as used herein means molecular weight as determined by molecular exclusion chromatography. These high molecular size antigens are immunoreactive to Type III-specific antibodies. It has further been found that still greater improvement can be achieved and higher yields of polysaccharide antigen obtained by culturing the organisms in a broth free from constituents having a molecular size above $10^5$ daltons, separating or harvesting the organisms from the broth after culturing, then recovering from the residual broth polysaccharides including a fraction having molecular sizes above $0.8 \times 10^6$. An additional but smaller quantity of the large molecular size polysaccharides can be obtained by extraction from the organisms as well. The same procedures, it has been found, can be used to prepare large molecular size antigens which are immunoreactive to Type Ia- and Type Ic-specific antibodies, and antigens having a molecular size from about $0.2 \times 10^6$ to about $6 \times 10^6$ daltons which are immunoreactive to Type II specific antibodies. The invention also relates to the injection of polysaccharide antigen or vaccine into a human to raise antibodies thereto in high titer, separating the antiserum from the blood of said human, and fractionating the antiserum to produce a gamma globulin fraction containing said antibodies.

It has been found that the amount of glucose present in conventional nutrient broth, e.g., 2 g/l as in Todd-Hewitt broth, is insufficient to permit maximum production of the polysaccharide antigen or vaccine, and that increases in the amount of glucose up to about 15 g/l effectively and progressively increase the production of antigen. Although the amount of glucose can be increased beyond 15 g/l without deleterious effects, there is no advantage obtained by exceeding this amount. Desirably, the amount of glucose in the broth is at least 10 g/l; preferably, the glucose concentration is from 14-16 g/l of broth.

When the amount of glucose in the broth is about 4 g/l or more, the pH of the nutrient broth cannot be effectively maintained within the range pH 6-8, more particularly within the preferred range pH 6.8-7.6, simply by adding buffer such as a conventional phosphate buffer to the broth when the organisms are introduced. As the large amount of glucose present is consumed by the organisms, the amount of acid liberated is so great that a buffer, even when present in very high concentration, tends to be swamped, the pH drops below 6, and the specificity of the immunogen produced is altered, apparently as a result of degradation of the polysaccharide. On the other hand, as the pH value is increased above pH 8, the growth rate of the organism falls of. Consequently, it has been found that intermittent or continuous introduction of alkaline material into the broth during growth of the organisms is required to maintain the pH within the specified range. The preferred alkaline material is sodium hydroxide although any strongly alkaline material such as sodium carbonate or ammonium hydroxide or carbonate also can be used. The alkaline material is most conveniently introduced in the form of an aqueous solution, particularly when a titrator is employed. The culturing can be carried out at any usual or convenient temperature, e.g., at about room temperature or somewhat above (20°-40° C.).

Under the foregoing conditions, culturing of Group B streptococci produces a polysaccharide antigen including a fraction having a molecular size of 0.8 to $6 \times 10^6$ daltons which can be extracted from the organisms after their separation from the nutrient broth by means of the previously known extraction procedure. However, it has been found that most of the polysaccharides are released by the organisms into the broth itself, so that much higher yields can be obtained by separating the organisms from the broth, then recovering the desired large molecular size ($0.8-6 \times 10^6$) and highly immunogenic polysaccharides from the residual broth. To facilitate this recovery, it has been found desirable to use a nutrient broth or culture medium free from constituents having molecular sizes above $10^5$ at the beginning of culturing, preferably free from constituents having molecular sizes above $3 \times 10^4$. Conventional nutrient broths for the culture of Group B streptococci contain infusions of animal tissue which include large molecular size constituents. For example, the conventionally used Todd-Hewitt broth contains as its principal ingredient filtered beef heart infusion. The large molecular size constituents, e.g., those above $10^5$ d, can be removed from the broth by any conventional fractionation or separation procedures such as dialysis, ultrafiltration, or chromatography. The remaining broth, containing only small molecular size ingredients including 5–15 g/l of glucose, is highly effective for culturing or propagating the Group B streptococci.

After removal or separation of the organisms from the broth, for example by centrifugal sedimentation, the large molecular size polysaccharide antigens produced can readily be recovered from the residual or supernatant broth and separated from the low molecular size constituents thereof by conventional fractionation or separation procedures such as those mentioned above. Moreover, additional polysaccharide antigens of the same large ($0.8$–$6 \times 10^6$) molecular size can be obtained by extraction of the organisms which are separated from the broth. The extraction can be accomplished by the procedures employed in the prior art for extracting small molecular size polysaccharides from Type III Group B streptococci. These procedures involve suspending the organisms at pH 6–8 for several hours at room temperature in an extraction medium comprising a saline buffer, preferably containing ethylene diamine tetraacetic acid sodium, and separating the organisms from the medium. However, any neutral aqueous buffer can be used.

The large molecular size polysaccharide antigens obtained from either the nutrient broth or from extraction of the organisms can be further purified by the usual ethanol precipitation followed by enzymatic degradation to remove nucleic acids and proteins, and by gel chromatography with 0.05 M Tris buffer at pH 7.3 to isolate the fraction having a molecular size above $0.8 \times 10^6$. Any other buffer at pH 6.5–8.0 can be used as well. The polysaccharide in this fraction is then subjected to salt-ethanol precipitation, resuspended in distilled water and lyophilized to yield dry solid polysaccharide antigen. In general, 1–8 mg purified Type III polysaccharide antigen is obtained from each liter of culture of Type III organism. The purified polysaccharide antigen contains as its main chemical constituents sialic acid, galactose, glucose, and glucosamine, and consists of the following repeating units:

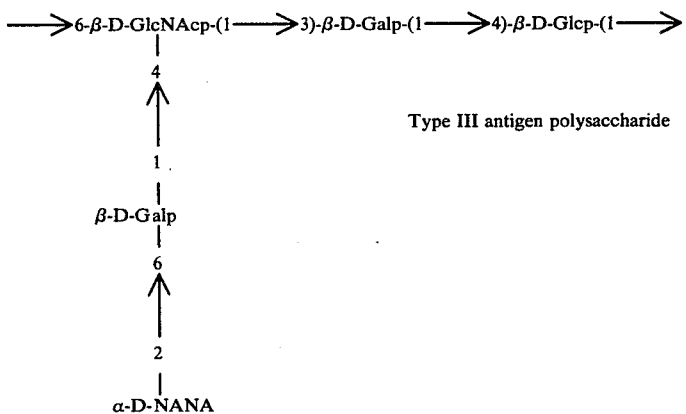

Type III antigen polysaccharide in which GlcNAcp stands for N-acetyl glucosamine (in the pyranose form), Galp stands for galactose (in the pyranose form), Glcp stands for glucose (in the pyranose form) and α-D-NANA stands for sialic acid. This polysaccharide antigen differs from that prepared by the method of the prior art in that it contains neither mannose nor heptose, whereas that prepared by the prior art procedure does contain both mannose and heptose.

When Type Ia or Ic or Type II Group B streptococci are subjected to the same procedures, there are obtained different purified soluble type specific polysaccharides, also containing as their principal constituents sialic acid, galactose, glucose and glucosamine.

The Types Ia and Ic antigens also have a molecular size above $0.8 \times 10^6$ and are obtained in approximately the same yield as is that from Type III.

The Type II polysaccharide antigen consists of the following repeating units:

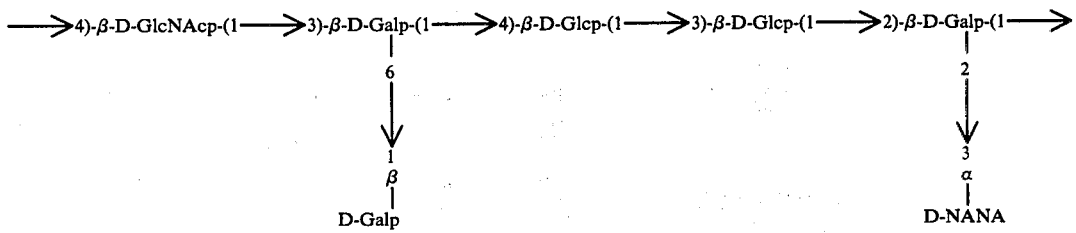

in which the symbols have the same meaning set forth above. This polysaccharide has a molecular size from about $0.2 \times 10^6$ to about $6 \times 10^6$ daltons.

The Types Ia and Ic, Type II, and Type III polysaccharide antigens are immunologically distinct, being readily distinguishable by capillary precipitin reactions with type-specific sera prepared to Group B streptococci of the respective serotype in accordance with conventional procedures as set forth by Lancefield, J. Experimental Medicine, Vol. 59, pages 441–458 (1934); ibid, Vol. 67, pages 25 et seq. (1938); and Wilkinson et al., Infection and Immunity, Vol. 4, pages 596 et seq. (1971).

For use as a vaccine, the purified polysaccharide antigen is suspended in pyrogen-free saline or any other physiologically acceptable non-toxic vehicle or medium, which may contain any conventional stabilizers or other additives, as desired. The concentration of antigen is not critical and may be varied over a wide range, but for many purposes a range of 10–1000 µg/ml is convenient and suitable. In this form it is stable during prolonged storage at 4° C. and is sterile, non-toxic, and non-pyrogenic when subjected to animal tests as prescribed by Food and Drug Administration Regulations (Title 21, Sec. 610.11–610.13). No biologically active endotoxin was found in the vaccine, and no systemic symptoms were observed in mice, guinea pigs, rabbits, or primates. No antibody formation was found upon injection of the vaccine into rabbits or primates.

A vaccine containing polysaccharides of intermediate molecular size ($5-6 \times 10^5$ daltons) can also be prepared even when the pH is allowed to drop below 6, as for example when a phosphate buffer is employed in the nutrient broth, and that vaccine is antigenic in a human being as described by Baker et al., J. Clin. Invest., Vol. 61, pages 1107–1110 (1978). Although such polysaccharides have different immunological properties from those of higher molecular size ($0.8-6 \times 10^6$) as set forth above, nevertheless, they have sufficiently high activity so that they can effectively be used as vaccines. They are also effective to raise sufficient antibody in selected vaccines so that it is possible, by isolating the gamma globulin fraction of the antisera, to obtain antibody of sufficiently high titer to be effective for use by injection of subjects to provide passive immunization.

The following specific examples will serve to illustrate more fully the nature of the present invention without acting as a limitation upon its scope.

EXAMPLES

Todd-Hewitt broth of the following composition was obtained from a commercial supplier:

| Ingredient | Grams/liter |
|---|---|
| Beef heart infusion (filtered) (solids) | 500 |
| Neopeptone (solids) | 20 |
| Dextrose | 2 |
| Sodium chloride | 2 |
| Disodium phosphate | 0.4 |
| Sodium carbonate | 2.5 |

The broth was subjected to dialysis against distilled water through a suitable membrane to separate from it all ingredients having molecular size above 100,000 d. It was then sterilized by autoclaving and there were dissolved in it an additional 14 g/l of sterile glucose.

The contents of a starter flask containing Type III Group B streptococci were inoculated into the broth and allowed to grow at room temperature while maintaining the pH of the broth continually within the range pH 6.8–7.6 by means of a pH titrator. When the amount of organisms was greater than $3 \times 10^8$ organisms/ml, the bacteria were harvested by centrifugation at 4° C.

The residual or supernatant broth was concentrated to 1/10 volume by ultrafiltration while retaining all material of molecular size greater than $10^5$ d, then dialyzed exhaustively against distilled water to remove small molecular size components. Cold absolute alcohol was added in an amount of 30% by volume and the precipitate or flocculate containing some extraneous nucleic acids separated by centrifugation. To the supernatant there was added 80% by volume of cold absolute alcohol and the precipitate containing the polysaccharides was separated by centrifugation. The solid pellet was dried, then suspended in a buffered solution containing 0.01 M Tris (hydroxymethyl aminomethane) hydrochloride, 0.001 M calcium chloride, and 0.001 M magnesium chloride at pH 7.3. This solution was then twice digested for three hours at 37° C. with ribonuclease and deoxyribonuclease at concentrations of 0.5 g/l, then twice with Pronase B at 1.0 g/l to destroy unwanted nucleic acids and proteins.

The enzyme-treated solution was then fractionated by chromatography on a column of Sepharose 4B equilibrated in 0.01 M Tris hydrochloride buffer at pH 7.3 to separate the fraction containing substances of small molecular size (below $10^5$). The large molecular size fractions ($8-11 \times 10^5$) were eluted, combined, and mixed with four volumes of absolute ethanol to precipitate the large molecular size polysaccharide which was separated by centrifugation, and lyophilized to provide a purified dry solid product consisting of repeating units of Type III antigen of the structure defined above. In general, each one liter lot of Type III organisms yielded about 5–15 mg of polysaccharide antigen (mw 0.8 to $5 \times 10^6$) by this procedure.

Smaller amounts of the same molecular weight antigen were obtainable by extraction of the harvested bacteria using the same procedures as employed in the prior art for lower molecular weight polysaccharide Type III antigens. In general each 1 liter of organisms yielded about 1–4 mg of the antigen by such procedure. Indeed, it has been found that lower molecular size fractions, as low as about $0.2 \times 10^6$ daltons, of the same Type III antigen having the chemical structure described above can be made by the same procedure and possesses the same immunoreactivity, which is different from that of the Type III polysaccharide antigen described in the prior art.

Following the same procedure but substituting other Group B streptococci for the Type III, there can be obtained other type-specific polysaccharide antigens. When Type Ia or Type Ic Group B streptococci are used in place of Type III, the purified large molecular size polysaccharide antigen obtained in dry solid form has a molecular size from about 0.2 to $5 \times 10^6$ d. When Type II Group B streptococci are used in place of Type III in the foregoing procedure, the purified large molecular size polysaccharide antigen obtained in dry solid form is composed of repeating units of the structure defined above for Type II antigens and having a molecular size from about 0.2 to about $6 \times 10^6$ d. It is immunologically distinct from both the Type I and the Type III polysaccharide antigens when examined by the procedures of Lancefield mentioned above.

For use as a vaccine, suspensions were prepared containing 100 µ/ml of the dried polysaccharide Types Ia and Ic, II, and III antigens, respectively, in a normal saline solution, and there was injected subcutaneously into each volunteer 0.5 ml. of one such suspension. Both Type III polysaccharide antigen of large molecular size prepared in accordance with the present invention and that of smaller molecular size ($5-6 \times 10^5$) exhibited high immunogenicity, developing from 0.1 to 2000 µg/ml antiserum of specific antibody in selected vaccines as determined by radioimmunoassay of the antiserum using as tracer polysaccharide antigens intrinsically labelled by the introduction of tritiated acetate into the nutrient broth.

Although occasional non-immunized human adults have very high levels of type-specific antibody in their sera, it would be necessary to screen very large populations to select those individuals whose plasma could be pooled to make sufficiently high titered globulin fractions to be useful for passive immunization. Several lots of pooled human gamma globulin from non-immunized adults have been assayed for anti-Types Ia and Ic, anti-Type II, and anti-Type III polysaccharide antibody and have been found to contain only 5–20 μg/ml of serum. Immunization by intravenous injection of such low titer globulins would require prohibitively large doses with attendant risk of adverse reactions.

Pools of human sera from selected individuals vaccinated with polysaccharide antigens having molecular size from $0.5$–$6 \times 10^6$ obtained from nutrient broth or by extraction of Type III organisms as described above are readily obtainable having specific antibody concentrations of 200 μg/ml or more. Similar pools of human sera are available from individuals vaccinated with Types Ia and Ic antigens or with Type II antigens. Such high titer pooled concentrated sera can readily be fractionated by conventional procedures to provide a globulin fraction containing most of the type-specific antibody and of sufficiently high activity, at least 2000 μg/ml of specific activity, so that the hyperimmune globulin is effective in small doses of 0.3–1 ml, preferably about 0.5 ml, when administered in a suitable physiologically acceptable carrier such as normal saline either intravenously or intramuscularly. The concentration of the globulin in the carrier may be from 5 to 20% by weight. The hyperimmune globulin can be administered either to pregnant women prior to delivery or to neonates to provide passive immunization.

Similar results can be obtained using other type-specific antigens for Group B streptococci prepared as described above.

What is claimed is:

1. In a method of making a polysaccharide vaccine against Group B streptococci which comprises culturing the streptococci in a nutrient broth the improvement which comprises introducing into the broth at least 10 g/l of glucose and maintaining the pH of the broth at pH 6–8 to provide polysaccharide antigen including a fraction having a molecular size above $0.8 \times 10^6$ d, and recovering said antigen from the broth.

2. A method as claimed in claim 1 in which the streptococci are Type III strain.

3. A method as claimed in claim 1 in which the streptococci are Type Ia or Type Ic strain.

4. A method as claimed in claim 1 in which the streptococci are Type II strain.

5. A method as claimed in claim 1 in which the pH is maintained by introducing alkaline material into the broth during the growth of said streptococci.

6. A method as claimed in claim 5 in which the streptococci are Type III strain.

7. A method as claimed in claim 5 in which the streptococci are Type Ia or Type Ic strain.

8. A method as claimed in claim 5 in which the streptococci are Type II strain.

9. A method as claimed in claim 5 in which the pH is maintained at pH 6.8 to 7.6.

10. A method as claimed in claim 5 in which the amount of glucose is from 14 to 16 g/l.

11. A method as claimed in claim 1 in which the nutrient broth is free from constituents having a molecular size above $10^5$ d at the beginning of culturing, and polysaccharide antigen including a fraction having a molecular size from 8 to $11 \times 10^5$ d recovered from the broth after harvesting of the streptococci.

12. A method of making a polysaccharide vaccine against Group B streptococci which comprises providing Todd-Hewitt broth, removing from said broth constituents having molecular sizes above $10^5$ d, adding glucose to said broth to provide a concentration of at least 10 g/l of glucose, culturing said streptococci in said broth while adding alkaline material to maintain the pH at pH 6–8, harvesting the streptococci from the broth, and separating from the residual broth polysaccharide antigens including a fraction having a molecular size above $0.8 \times 10^6$ d.

13. A method as claimed in claim 12 in which the streptococci are Type III strain.

14. A method as claimed in claim 12 in which the streptococci are Type Ia or Type Ic strain.

15. A method as claimed in claim 12 in which the streptococci are Type II strain.

16. A method as claimed in claim 12 in which there is removed from the broth constituents having molecular sizes above $3 \times 10^4$ d, and an amount of glucose is added to provide a concentration of 14 to 16 g/l.

17. A method as claimed in claim 16 in which the streptococci are Type III strain.

18. A method as claimed in claim 16 in which the streptococci are Type Ia or Type Ic strain.

19. A method as claimed in claim 16 in which the streptococci are Type II strain.

* * * * *